(12) United States Patent
Shen et al.

(10) Patent No.: US 9,715,729 B2
(45) Date of Patent: Jul. 25, 2017

(54) METHOD AND APPARATUS FOR PROCESSING BLOCK TO BE PROCESSED OF URINE SEDIMENT IMAGE

(71) Applicant: Siemens Healthcare Diagnostics Inc., Tarrytown, NY (US)

(72) Inventors: Tian Shen, Xi An (CN); Juan Xu, Beijing (CN); XiaoFan Zhang, Charlotte, NC (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 0 days.

(21) Appl. No.: 15/306,883

(22) PCT Filed: Apr. 30, 2015

(86) PCT No.: PCT/US2015/028438
§ 371 (c)(1),
(2) Date: Oct. 26, 2016

(87) PCT Pub. No.: WO2015/168365
PCT Pub. Date: Nov. 5, 2015

(65) Prior Publication Data
US 2017/0053400 A1    Feb. 23, 2017

(30) Foreign Application Priority Data
Apr. 30, 2014    (CN) .......................... 2014 1 0183548

(51) Int. Cl.
*G06K 9/00*    (2006.01)
*G06T 7/00*    (2017.01)
(Continued)

(52) U.S. Cl.
CPC ......... *G06T 7/0012* (2013.01); *G01N 33/493* (2013.01); *G06K 9/4647* (2013.01);
(Continued)

(58) Field of Classification Search
CPC . G01N 33/493; G06K 2209/05; G06T 7/0012
See application file for complete search history.

(56) References Cited

U.S. PATENT DOCUMENTS 5,463,702 A * 10/1995 Trueblood ................ G06T 9/00
348/391.1
5,768,412 A * 6/1998 Mitsuyama ........ G06K 9/00127
382/133
(Continued)

OTHER PUBLICATIONS

International Search Report and Written Opinion of International Application No. PCT/US2015/028438 dated Aug. 12, 2015.
(Continued)

*Primary Examiner* — Gandhi Thirugnanam
(74) *Attorney, Agent, or Firm* — Kyle D. Petaja (57) ABSTRACT

Concepts herein relate to processing urine sediment images. An example method comprises: approximating the color of a pixel in a block to be processed to one of the $k_c$ colors in a code book, wherein the code book is a set of the $k_c$ colors generated in a set of urine sample blocks; obtaining a distribution histogram of the number of pixels the color approximation results of which fall on each color of the $k_c$ colors; using an occurrence frequency correction factor to correct the number of pixels the color approximation results; standardizing the corrected number of pixels the color approximation results; and processing the block to be processed.

16 Claims, 2 Drawing Sheets

(51) Int. Cl.
  *G01N 33/493* (2006.01)
  *G06K 9/46* (2006.01)
  *G06K 9/62* (2006.01)
  *G06T 7/40* (2017.01)

(52) U.S. Cl.
  CPC .......... *G06K 9/6218* (2013.01); *G06T 7/0081* (2013.01); *G06T 7/408* (2013.01); *G06K 2209/05* (2013.01); *G06T 2207/10024* (2013.01); *G06T 2207/10056* (2013.01); *G06T 2207/20081* (2013.01); *G06T 2207/30004* (2013.01); *G06T 2207/30024* (2013.01)

(56) References Cited

U.S. PATENT DOCUMENTS

| | | | | |
|---|---|---|---|---|
| 5,911,002 | A * | 6/1999 | Mitsuyama | G01N 33/493 382/156 |
| 2005/0251347 | A1* | 11/2005 | Perona | G06K 9/00134 702/19 |
| 2007/0014435 | A1* | 1/2007 | Mirowski | G01V 11/00 382/109 |
| 2010/0246926 | A1* | 9/2010 | Patel | G06K 9/0014 382/133 |
| 2011/0002516 | A1* | 1/2011 | Manri | G01N 15/147 382/128 |
| 2011/0169837 | A1* | 7/2011 | Takata | G01N 15/14 345/440.2 |
| 2012/0134559 | A1* | 5/2012 | Suzuki | G01N 15/1404 382/128 |
| 2013/0011042 | A1* | 1/2013 | Satish | G06K 9/00 382/134 |
| 2013/0121546 | A1* | 5/2013 | Guissin | G06T 7/0012 382/128 |
| 2017/0053399 | A1* | 2/2017 | Xu | G06T 7/0012 |
| 2017/0053400 | A1* | 2/2017 | Shen | G06T 7/0012 |

OTHER PUBLICATIONS

Meer et al.,"Edge Detection with Embedded Confidence", Dec. 2001, IEEE Transactions on Pattern Analysis and Machine Intelligence, vol. 23, No. 12, pp. 1351-1365.

Comaniciu et al.,"Mean Shift: A Robust Approach Toward Feature Space Analysis", May 2002, IEEE Transactions on Pattern Analysis and Machine Intelligence, vol. 24 Issue 5, p. 603-619.

Perronnin et al.,"Improving the Fisher Kernel for Large-Scale Image Classification", 2010—European Conference on computer Vision, Sep. 2010, pp. 1-15.

Wengert et al., "Bag-of-colors for improved image search", Nov. 2011,19th ACM International Conference on Multimedia, pp. 1-5.

Swain et al., "Color Indexing", 1991, International Journal of Computer Vision, 7:1, pp. 11-32.

* cited by examiner

*Fig. 3*

METHOD AND APPARATUS FOR PROCESSING BLOCK TO BE PROCESSED OF URINE SEDIMENT IMAGE

The subject application claims benefit under 35 USC §119(e) of Chinese Patent Application No. 201410183548.4, filed Apr. 30, 2014. The entire contents of the above-referenced patent application are hereby expressly incorporated herein by reference.

TECHNICAL FIELD

The present invention relates to biological detection, and in particular to a method and apparatus for processing a block to be processed of a urine sediment image.

BACKGROUND ART

In common urine sediment analysis, first, a urine sample image is shot using a microscope imaging system. Then, the candidate blocks in the urine sample image are segmented using, for example, edge detection technology. By removing obvious background blocks from these candidate blocks, blocks to be processed are detected. Next, the blocks to be processed are processed.

Currently, there are mainly two ways of processing the blocks to be processed. The first is classification, i.e. directly classifying these blocks to be processed into various visible element (such as cast, epithelium and erythrocyte) blocks and background blocks that are easy to confuse with visible elements. The second is block retrieval, which does not directly classify the blocks to be processed but retrieves blocks similar to the previously stored blocks to be processed in a database. The unique difference with regard to the result of classification lies in that block retrieval may retrieve a plurality of similar blocks to be provided to a user, and thus can provide more information for the user. The user may perform a further selection or judgement in the plurality of similar blocks.

Currently, classification and block retrieval via machine automatically generally use an approach of machine learning. Several features for classification or block retrieval are specified and constitute a feature set. A large number of training sample blocks are firstly used to constitute a training sample set for training a processing model (a classification model or a block retrieval model). With regard to each training sample block in the training sample set, the features in the feature set are calculated for the processing model to learn. In this way, when the trained processing model receives a new block to be processed, the features in the feature set are calculated for the new block to be processed, and with reference to the previous training result, classification can be performed on the new block to be processed or the previously stored similar images are retrieved therefor.

CONTENTS OF THE INVENTION

One embodiment of the present invention aims to improve the precision of processing a block to be processed.

According to one embodiment of the present invention, a method for processing a block to be processed of a urine sediment image is provided, comprising: approximating the color of a pixel in a block to be processed to one of the kc colors in a code book, wherein the code book is a set of the kc colors generated in a set of urine sample blocks, the kc colors are formed by clustering the colors extracted from the urine sample blocks in the set, and kc is a positive integer; obtaining a distribution histogram of the number of pixels the color approximation results of which fall on each color of the kc colors in the block to be processed; using an occurrence frequency correction factor to correct the number of pixels the color approximation results of which fall on each color in the distribution histogram; standardizing the corrected number of pixels the color approximation results of which fall on each color in the distribution histogram; and by way of taking the standardized distribution histogram as a feature in a feature set of block processing, processing the block to be processed.

In a particular implementation, processing a block to be processed of a urine sediment image comprises either of the following: classifying the block to be processed; and performing block retrieval on the block to be processed.

In a particular implementation, the step of generating a code book from a set of urine sample blocks comprises: converting a urine sample block in the set from an RGB color space into a Lab color space; segmenting the urine sample block converted into the Lab color space into a plurality of regions; selecting h pixels in each region of the plurality of regions after segmentation, where h is a positive integer; and clustering the colors of the selected h pixels into one of the kc colors.

In a particular implementation, the step of segmenting the urine sample block converted into the Lab color space into a plurality of regions comprises: using a mean-shift algorithm to segment the urine sample block converted into the Lab color space into a plurality of regions, wherein the area Amin of a minimum region in the urine sample block converted into the Lab color space is adjustable; and h=ceil (RegionArea/SampleRatio), where RegionArea is the area of a specific region in the plurality of regions after segmentation, h is the number of pixels selected in the specific region, SampleRatio is equal to a specified number of Amin, and ceil ( ) is a round-up function.

In a particular implementation, the step of approximating the color of a pixel in a block to be processed to one of the kc colors in a code book comprises: converting the block to be processed from an RGB color space into a Lab color space; calculating an Euclidean distance of the color of the pixel in the block to be processed to the kc colors respectively; and approximating the color of the pixel in the block to be processed to a color corresponding to a minimum Euclidean distance in the kc colors.

In a particular implementation, the occurrence frequency correction factor is obtained from a set of training sample blocks, wherein if it is assumed that the number of training sample blocks in the set of training sample blocks is D, and there are di training sample blocks containing pixels of the ith color in the code book, then an occurrence frequency correction factor of the ith color idf $(i)=\log(D/di)$; and the step of using an occurrence frequency correction factor to correct the number of pixels the color approximation results of which fall on each color in the distribution histogram comprises: multiplying the number of pixels the color approximation results of which fall on the ith color in the distribution histogram by the occurrence frequency correction factor idf $(i)$ of the ith color.

In a particular implementation, the step of standardizing the corrected number of pixels the color approximation results of which fall on each color in the distribution histogram comprises: taking a square root of the corrected number of pixels the color approximation results of which fall on each color in the distribution histogram and then performing standardization.

According to one embodiment of the present invention, an apparatus for processing a block to be processed of a urine sediment image is provided, comprising: an approximation unit configured to approximate the color of a pixel in a block to be processed to one of the kc colors in a code book, wherein the code book is a set of the kc colors generated in a set of urine sample blocks, the kc colors are formed by clustering the colors extracted from the urine sample blocks in the set, and kc is a positive integer; an obtaining unit configured to obtain a distribution histogram of the number of pixels the color approximation results of which fall on each color of the kc colors in the block to be processed; a correction unit configured to use an occurrence frequency correction factor to correct the number of pixels the color approximation results of which fall on each color in the distribution histogram; a standardization unit configured to standardize the corrected number of pixels the color approximation results of which fall on each color in the distribution histogram; and a processing unit configured to, by way of taking the standardized distribution histogram as a feature in a feature set of block processing, process the block to be processed.

In a particular implementation, the apparatus is used for either of the following: classifying the block to be processed; and performing block retrieval on the block to be processed.

In a particular implementation, a generation unit is further configured to: convert a urine sample block in the set from an RGB color space into a Lab color space; segment the urine sample block converted into the Lab color space into a plurality of regions; select h pixels in each region of the plurality of regions after segmentation, where h is a positive integer; and cluster the colors of the selected h pixels into one of the kc colors.

In a particular implementation, segmenting the urine sample block converted into the Lab color space into a plurality of regions is achieved by using a mean-shift algorithm, wherein the area Amin of a minimum region in the urine sample block converted into the Lab color space is adjustable. h=ceil (RegionArea/SampleRatio), where RegionArea is the area of a specific region in the plurality of regions after segmentation, h is the number of pixels selected in the specific region, SampleRatio is equal to a specified number of Amin, and ceil ( ) is a round-up function.

In a particular implementation, the approximation unit is further configured to: convert the block to be processed from an RGB color space into a Lab color space; calculate an Euclidean distance of the color of the pixel in the block to be processed to the kc colors respectively; and approximate the color of the pixel in the block to be processed to a color corresponding to a minimum Euclidean distance in the kc colors.

In a particular implementation, the occurrence frequency correction factor is obtained from a set of training sample blocks, wherein if it is assumed that the number of training sample blocks in the set of training sample blocks is D, and there are di training sample blocks containing pixels of the ith color in the code book, then an occurrence frequency correction factor of the ith color idf (i)=log (D/di). The correction unit is further configured to: multiply the number of pixels the color approximation results of which fall on the ith color in the distribution histogram by the occurrence frequency correction factor idf (i) of the ith color.

In a particular implementation, the standardization unit is further configured to: take a square root of the corrected number of pixels the color approximation results of which fall on each color in the distribution histogram and then perform standardization.

A feature in a feature set in the prior art focuses relatively more on shape and space information. However, some types of visible elements (such as a leukocyte) often have many variants, and therefore there is a great intra-class difference, and some different types of visible elements show a relatively great inter-class similarity. In addition, the visible elements are not always located in the center of a block, and a feature that is relatively dependent on space information may worsen the processing result. Therefore, the precision of processing a block to be processed is not high in the prior art. Since the feature used in the embodiments of the present invention is calculated based on the color of a pixel in a block to be processed, the feature is not influenced by the change in shape or space information of a visible element, and thus a relatively high processing precision can still be obtained under the condition where some visible elements differ or change location.

In addition, compared with a shape feature and a texture feature, it is easier to perform calculation based on the feature of a color, thereby improving the speed of processing.

Since the code book in the embodiments of the present invention is generated by training a set of urine sample blocks rather than prespecification, a color of the code book surely represents a color frequently appearing in a block of a urine sediment image so that the processing result further reflects objective reality, thereby improving processing precision.

Since the embodiments of the present invention also use an occurrence frequency correction factor to correct the number of pixels the color approximation results of which fall on each color in a distribution histogram and then perform standardization, the dominance of a color that appears frequently over a color that does not appear frequently in the final processing result is relieved, which dominance may worsen processing performance.

In the embodiments of the present invention, when a code book is generated from a set of urine sample blocks, a urine sample block in the set is converted from an RGB color space into a Lab color space, and a mean-shift algorithm is used to segment the urine sample block converted into the Lab color space into a plurality of regions, wherein the mean-shift algorithm does not segment the urine sample block into a plurality of regions with the same size but specifies a relatively large region for a background portion containing less useful information so as to select pixels that are relatively sparse, and specifies a relatively small region for useful details of the urine sample block with a relatively large amount of information so as to select pixels that are relatively intense, and thus the embodiments of the present invention improve the efficiency of collecting useful information.

DESCRIPTION OF THE ACCOMPANYING DRAWINGS

These and other features and advantages of the present invention will become more apparent by way of the detailed description hereinbelow in conjunction with the accompanying drawings.

DETAILED DESCRIPTION OF EMBODIMENTS

Various embodiments of the present invention will be described below in detail in combination with the accompanying drawings.

Figure 1:
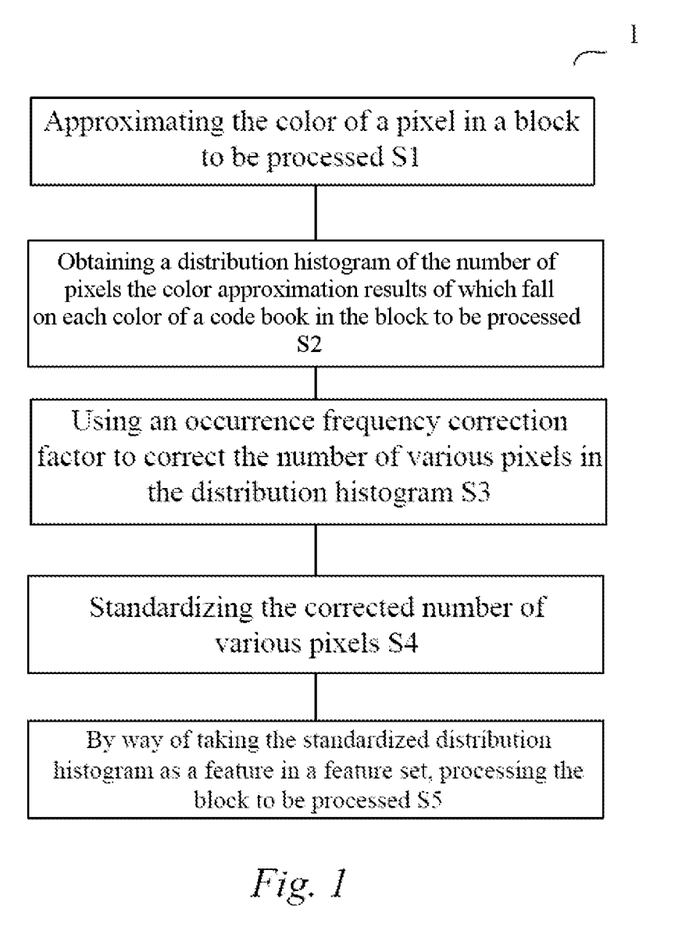
FIG. 1 shows a flowchart of a method for processing a block to be processed of a urine sediment image according to one embodiment of the present invention.

FIG. 1 shows a flowchart of a method 1 for processing a block to be processed of a urine sediment image according to one embodiment of the present invention.

In step S1, the color of a pixel in a block to be processed is approximated to one of the kc colors in a code book. The code book is a set of the kc colors generated in a set of urine sample blocks, the kc colors are formed by clustering the colors extracted from the urine sample blocks in the set, and kc is a positive integer.

The code book needs to be generated from a set containing a certain number of urine sample blocks. The selection of these urine sample blocks are, for example, random, and the number of the blocks must be enough so as to basically cover the colors that frequently appear in urine sample blocks generally. The detailed process of generating a code book is described as follows.

Firstly, a urine sample block in the set is converted from a three-primary-color light (RGB) color space into a Lab color space. The Lab color space is a color-opponent space, where a dimension L represents lightness, and dimensions a and b represent color opponent dimensions. The conversion from the three-primary-color light (RGB) color space to the Lab color space means converting from R, G and B dimensions into L, a and b dimensions. This can be achieved by converting the values of the R, G and B dimensions of the pixel value of each pixel in a urine sample block into the values of the L, a and b dimensions. Experiments show that the conversion from the RGB color space to the Lab color space contributes to improving processing precision.

Then, a mean-shift algorithm is used to segment the urine sample block converted into the Lab color space into a plurality of regions, wherein the area Amin of a minimum region in the urine sample block converted into the Lab color space is adjustable. The mean-shift algorithm is a known algorithm. In the algorithm, the value of the area Amin of a minimum region in the urine sample block converted into the Lab color space is prespecified by a user as an input. The algorithm can segment out a plurality of regions with unequal sizes, and the sizes of these regions are more or less related to the information contained therein. For example, background portions with a large area are all similar, the less information is contained, and a relatively large region can be specified for the background portions. A mean-shift algorithm does not segment a urine sample block into a plurality of regions with the same size but specifies a relatively large region for a background portion containing less useful information so as to select pixels that are relatively sparse, and specifies a relatively small region for useful details of the urine sample block with a relatively large amount of information so as to select pixels that are relatively intense, thus improving the efficiency of collecting useful information.

Then, h pixels are selected in each region of the plurality of regions after segmentation, where h is a positive integer. h=ceil (RegionArea/SampleRatio). RegionArea is the area of a specific region in the plurality of regions after segmentation. h is the number of pixels selected in the specific region. SampleRatio is set as three to four times Amin. ceil ( ) is a round-up function. Since Amin is specified and RegionArea of each region is not fixed, h calculated for each region is also not fixed.

After some pixels are selected in each region after segmentation, the colors of the pixels selected in each region after segmentation in each urine sample block in the set are gathered. The gathered colors are clustered. It is known that there are many clustering methods. The result of clustering is to cluster the colors of the selected pixels into one of the kc colors and thus form a code book containing kc colors. Since the kc colors in the code book are all generated by training actual urine sample blocks, the processing result further reflects objective reality.

The process of approximating the color of a pixel in a block to be processed to one of the kc colors in a code book is described as follows.

Firstly, the block to be processed is converted from an RGB color space into a Lab color space. That is to say, each pixel value of the block to be processed is converted from a value of the RGB color space into a value of the Lab color space.

Then, the Euclidean distances of the color of a certain pixel in the block to be processed to the kc colors are calculated respectively, and the color of the pixel is approximated to a color corresponding to a minimum Euclidean distance in the kc colors. That is to say, when a color in the kc colors has the minimum Euclidean distance to the color of the pixel, the color of the pixel is approximated to this color. Thus, the colors of each pixel in the block to be processed are all approximated to one of the kc colors. The calculation method of Euclidean distance is known.

After the colors of each pixel in the block to be processed are all approximated to one of the kc colors, how many pixels with colors approximated to the first color, how many pixels with colors approximated to the second color, . . . and how many pixels with colors approximated to the kcth color in the block to be processed can be counted so as to obtain a distribution histogram of the number of pixels the color approximation results of which fall on each color of the kc colors in the block to be processed in step S2.

In step S3, an occurrence frequency correction factor is used to correct the number of pixels the color approximation results of which fall on each color in the distribution histogram. The process of generating an occurrence frequency correction factor is introduced below.

As stated in the background art, with regard to classification or block retrieval achieved by a processing model, a large number of training sample blocks are firstly used to constitute a training sample set for training the processing model. With regard to each training sample block in the training sample set, the features in the feature set are calculated for the processing model to learn. In this way, when the trained processing model receives a new block to be processed, classification can be performed thereon or the previously stored similar images are retrieved therefor. This training sample set may be different from a set of urine sample blocks for generating a code book and is also different from actual blocks to be processed.

It is assumed that the number of training sample blocks in a training sample block set is D. With regard to each pixel of each training sample block, according to the method in step S1, these are approximated to one of the kc colors. Thus, it can be known how many training sample blocks in a training sample set have pixels with specific colors in a code book. It is assumed that there are di training sample blocks containing pixels of the ith color in the code book, and so an occurrence frequency correction factor of the ith color idf (i)=log (D/di). Therefore, with regard to each color in a code book, an occurrence frequency correction factor thereof is obtained through the above-mentioned training process.

Thus, in step S3, the number of pixels the color approximation results of which fall on the ith color in the distribution histogram is multiplied by the occurrence frequency correction factor idf (i) of the ith color which is obtained through the above-mentioned training process in advance so as to correct the number of pixels the color approximation results of which fall on each color in the distribution histogram. The dominance of a color that appears frequently over a color that does not appear frequently in the final processing result is relieved.

In step S4, a square root is taken of the corrected number of pixels the color approximation results of which fall on each color in the distribution histogram and then standardization is performed. The standardization usually has two approaches, L1-type standardization and L2-type standardization.

L1-type standardization can be performed with the following formula:

$$\overline{H}(i) = \frac{H(i)}{\sum_{i=1}^{k_c} |H(i)|} \quad \text{formula 1}$$

H(i) is the number of pixels the color approximation results of which fall on the ith color in the distribution histogram after correction and taking a square root, and $\overline{H}(i)$ is a standardization result of H(i).

L2-type standardization can be performed with the following formula:

$$\overline{H}(i) = \frac{H(i)}{\sqrt{\sum_{i=1}^{k_c} H^2(i)}} \quad \text{formula 2}$$

H(i) is the number of pixels the color approximation results of which fall on the ith color in the distribution histogram after correction and taking a square root, and $\overline{H}(i)$ is a standardization result of H(i).

Experiments show that with respect to L2-type standardization, $\overline{H}(i)$ obtained with L1-type standardization has a better processing performance when processing a block to be processed.

In step S5, by way of taking the standardized distribution histogram as a feature in a feature set of block processing, the block to be processed is processed. The particular process is that, for example, the above-mentioned training sample set composed of a large number of training sample blocks is firstly used for training a processing model. With regard to each training sample block in the training sample set, the standardized distribution histogram mentioned above is calculated through the above-mentioned steps S2-S5 as a feature in the feature set for the processing model to learn. When the trained processing model receives a new block to be processed, the standardized distribution histogram of the new block to be processed is calculated through the above-mentioned steps S2-S5. Since the processing model has learnt the standardized distribution histogram of each training sample block in a training sample set, the processing model can process a block to be processed (e.g. classification or retrieval of similar images).

Other Variants

Although in the above-mentioned embodiments, the processing of a block to be processed is described using classifying the block to be processed and performing block retrieval on the block to be processed as an example, those skilled in the art should understand that the processing method in the above-mentioned embodiments is also applicable to other processing that may appear currently or in the future and needs to analyse the features of the block to be processed.

Although in the above-mentioned embodiments, the generation of a code book is achieved through a specific process, it can also be achieved through other processes that can be understood by those skilled in the art, for example, a code book covering the colors that may usually appear in a block of a urine sediment image can also be generated by way of selecting pixels evenly at intervals on a urine sample block and clustering the colors thereof into one of the kc colors.

Although in the above-mentioned embodiments, SampleRatio is equal to three to four times Amin, actually, other multiples specified according to the requirements can also be used.

Although in the above-mentioned embodiments, a mean-shift algorithm is used to segment the urine sample block converted into a Lab color space into a plurality of regions, other algorithms known to those skilled in the art can also be used for segmentation. Although a formula h=ceil (RegionArea/SampleRatio) is taken as an example, h can also be specified by a user or be determined in other manners.

Although in the above-mentioned embodiments, approximating the color of a pixel in a block to be processed to one of the kc colors is performed using a minimum Euclidean distance approach, it can also be performed with other approaches (e.g. a maximum correlation coefficient). In addition, in the process of approximating the color of a pixel in a block to be processed to one of the kc colors, the conversion of the block to be processed from an RGB color space to a Lab color space may also not be performed.

A formula idf (i)=log (D/di) reflects the degree of frequency with which the ith color appears in a block of a urine sediment image. Although in the above-mentioned embodiments, an occurrence frequency correction factor of the ith color is calculated through the formula idf (i)=log (D/di), other formulas can also be designed if they can reflect the degree of frequency with which the ith color appears in the block of the urine sediment image.

Although in the above-mentioned embodiments, using an occurrence frequency correction factor to correct the number of pixels the color approximation results of which fall on each color in the distribution histogram is achieved by multiplying the number of pixels the color approximation results of which fall on the ith color in the distribution histogram by the occurrence frequency correction factor idf (i) of the ith color, other correction approaches can also be used. For example, the number of pixels the color approximation results of which fall on the ith color in the distribution histogram is multiplied by the square of the occurrence frequency correction factor idf (i) of the ith color so as to expand the influence of the occurrence frequency correction factor.

Although in the above-mentioned embodiments, a square root is taken of the corrected number of pixels the color approximation results of which fall on each color in the distribution histogram and then standardization is performed, standardization can be performed directly without taking the square root.

Although in the standardization of the above-mentioned embodiments, L1-type standardization and L2-type standardization are mentioned, and L1-type standardization is preferably used, actually, other standardization approaches known in the art can also be used.

Figure 2:
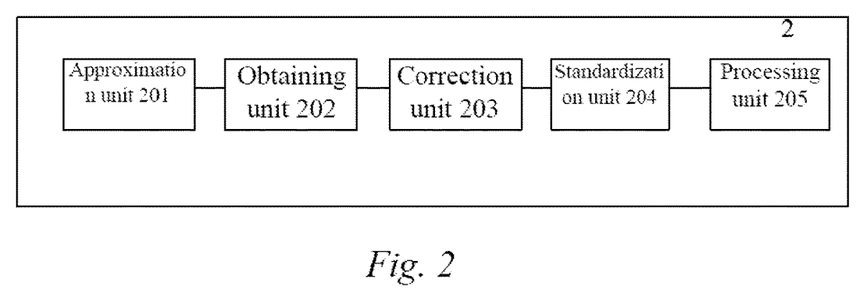
FIG. 2 shows a block diagram of an apparatus for processing a block to be processed of a urine sediment image according to one embodiment of the present invention.

As shown in FIG. 2, an apparatus 2 for processing a block to be processed of a urine sediment image according to one embodiment of the present invention comprises an approximation unit 201, an obtaining unit 202, a correction unit 203, a standardization unit 204 and a processing unit 205. The approximation unit 201 is configured to approximate the color of a pixel in a block to be processed to one of the kc colors in a code book, wherein the code book is a set of the kc colors generated in a set of urine sample blocks, the kc colors are formed by clustering the colors extracted from the urine sample blocks in the set, and kc is a positive integer. The obtaining unit 202 is configured to obtain a distribution histogram of the number of pixels the color approximation results of which fall on each color of the kc colors in the block to be processed. The correction unit 203 is configured to use an occurrence frequency correction factor to correct the number of pixels the color approximation results of which fall on each color in the distribution histogram. The standardization unit 204 is configured to standardize the corrected number of pixels the color approximation results of which fall on each color in the distribution histogram. The processing unit 205 is configured to, by way of taking the standardized distribution histogram as a feature in a feature set of block processing, process the block to be processed.

In addition, the apparatus 2 may be used for either of the following: classifying the block to be processed; and performing block retrieval on the block to be processed.

In addition, the code book can be generated from a set of urine sample blocks as follows: converting a urine sample block in the set from an RGB color space into a Lab color space; segmenting the urine sample block converted into the Lab color space into a plurality of regions; selecting h pixels in each region of the plurality of regions after segmentation, where h is a positive integer; and clustering the colors of the selected h pixels into one of the kc colors.

In addition, segmenting the urine sample block converted into the Lab color space into a plurality of regions may be achieved by using a mean-shift algorithm, wherein the area Amin of a minimum region in the urine sample block converted into the Lab color space is adjustable. h=ceil (RegionArea/SampleRatio), where RegionArea is the area of a specific region in the plurality of regions after segmentation, h is the number of pixels selected in the specific region, SampleRatio is equal to a specified number of Amin, and ceil ( ) is a round-up function.

In addition, the approximation unit may be further configured to: convert the block to be processed from an RGB color space into a Lab color space; calculate an Euclidean distance of the color of the pixel in the block to be processed to the kc colors respectively; and approximate the color of the pixel in the block to be processed to a color corresponding to a minimum Euclidean distance in the kc colors.

In addition, the occurrence frequency correction factor may be obtained from a set of training sample blocks which is different from a set of urine sample blocks, wherein if it is assumed that the number of training sample blocks in the set of training sample blocks is D and there are di training sample blocks containing pixels of the ith color in the code book, then an occurrence frequency correction factor of the ith color idf (i)=log (D/di). The correction unit may be further configured to: multiply the number of pixels the color approximation results of which fall on the ith color in the distribution histogram by the occurrence frequency correction factor idf (i) of the ith color.

In addition, the standardization unit may be further configured to: take a square root of the corrected number of pixels the color approximation results of which fall on each color in the distribution histogram and then performing standardization.

Figure 3:
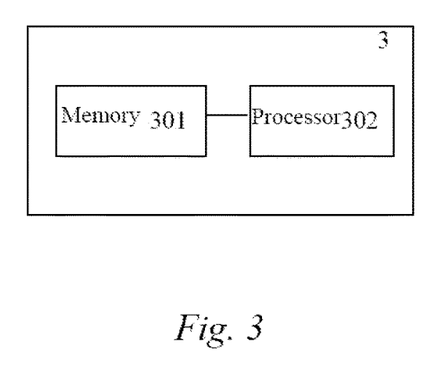
FIG. 3 shows a block diagram of a device for processing a block to be processed of a urine sediment image according to one embodiment of the present invention.

FIG. 3 shows a device 3 for processing a block to be processed of a urine sediment image according to one embodiment of the present invention. The device 3 may comprise a memory 301 and a processor 302. The memory 301 is used for storing an executable instruction. The processor 302 is used for performing an operation performed in each unit in the apparatus 2 according to the executable instruction stored in the memory.

In addition, one embodiment of the present invention further provides a machine-readable medium on which an executable instruction is stored; when the executable instruction is executed, a machine is caused to perform an operation performed by the processor 302.

Those skilled in the art should understand that various variations and modifications can be made to the above various embodiments without departing from the spirit of the present invention. Therefore, the scope of protection of the present invention should be defined by the appended claims.

The invention claimed is:

1. A method for processing a block to be processed of a urine sediment image, comprising:
  approximating the color of a pixel in a block to be processed to one of the $k_c$ colors in a code book, wherein the code book is a set of the $k_c$ colors generated in a set of urine sample blocks, the $k_c$ colors are formed by clustering the colors extracted from the urine sample blocks in the set, and $k_c$ is a positive integer;
  obtaining a distribution histogram of the number of pixels the color approximation results of which fall on each color of the $k_c$ colors in the block to be processed;
  using an occurrence frequency correction factor to correct the number of pixels the color approximation results of which fall on each color in the distribution histogram;
  standardizing the corrected number of pixels the color approximation results of which fall on each color in the distribution histogram; and
  by way of taking the standardized distribution histogram as a feature in a feature set of block processing, processing the block to be processed.

2. The method according to claim 1, characterized in that processing a block to be processed of a urine sediment image comprises either of the following:
  classifying the block to be processed; and
  performing block retrieval on the block to be processed.

3. The method according to claim 1, characterized in that the code book is generated from a set of urine sample blocks as follows:
  converting a urine sample block in the set from an RGB color space into a Lab color space;
  segmenting the urine sample block converted into the Lab color space into a plurality of regions;
  selecting h pixels in each region of the plurality of regions after segmentation, where h is a positive integer; and
  clustering the colors of the selected h pixels into one of the $k_c$ colors.

4. The method according to claim 3, characterized in that the step of segmenting the urine sample block converted into the Lab color space into a plurality of regions comprises: using a mean-shift algorithm to segment the urine sample block converted into the Lab color space into a plurality of regions, wherein the area $A_{min}$ of a minimum region in the urine sample block converted into the Lab color space is adjustable; and     h=ceil (RegionArea/SampleRatio), where RegionArea is the area of a specific region in the plurality of regions after segmentation, h is the number of pixels selected in the specific region, SampleRatio is equal to a specified multiple of $A_{min}$, and ceil ( ) is a round-up function.

5. The method according to claim 1, characterized in that the step of approximating the color of a pixel in a block to be processed to one of the $k_c$ colors in a code book comprises:

converting the block to be processed from an RGB color space into a Lab color space;

calculating an Euclidean distance of the color of the pixel in the block to be processed to the $k_c$ colors respectively; and     approximating the color of the pixel in the block to be processed to a color corresponding to a minimum Euclidean distance in the $k_c$ colors.

6. The method according to claim 1, characterized in that the occurrence frequency correction factor is obtained from a set of training sample blocks, wherein if it is assumed that the number of training sample blocks in the set of training sample blocks is D, and there are $d_i$ training sample blocks containing pixels of the ith color in the code book, then an occurrence frequency correction factor of the ith color idf (i)=log ($D/d_i$); and     the step of using an occurrence frequency correction factor to correct the number of pixels the color approximation results of which fall on each color in the distribution histogram comprises: multiplying the number of pixels the color approximation results of which fall on the ith color in the distribution histogram by the occurrence frequency correction factor idf (i) of the ith color.

7. The method according to claim 1, characterized in that the step of standardizing the corrected number of pixels the color approximation results of which fall on each color in the distribution histogram comprises: taking a square root of the corrected number of pixels the color approximation results of which fall on each color in the distribution histogram and then performing standardization.

8. An apparatus for processing a block to be processed of a urine sediment image, comprising:

an approximation unit configured to approximate the color of a pixel in a block to be processed to one of the $k_c$ colors in a code book, wherein the code book is a set of the $k_c$ colors generated in a set of urine sample blocks, the $k_c$ colors are formed by clustering the colors extracted from the urine sample blocks in the set, and $k_c$ is a positive integer;

an obtaining unit configured to obtain a distribution histogram of the number of pixels the color approximation results of which fall on each color of the $k_c$ colors in the block to be processed;

a correction unit configured to use an occurrence frequency correction factor to correct the number of pixels the color approximation results of which fall on each color in the distribution histogram;

a standardization unit configured to standardize the corrected number of pixels the color approximation results of which fall on each color in the distribution histogram; and     a processing unit configured to, by way of taking the standardized distribution histogram as a feature in a feature set of block processing, process the block to be processed.

9. The apparatus according to claim 8, characterized in that the apparatus is used for either of the following:

classifying the block to be processed; and performing block retrieval on the block to be processed.

10. The apparatus according to claim 8, characterized in that the code book is generated from a set of urine sample blocks as follows:

converting a urine sample block in the set from an RGB color space into a Lab color space;

segmenting the urine sample block converted into the Lab color space into a plurality of regions;

selecting h pixels in each region of the plurality of regions after segmentation, where h is a positive integer; and     clustering the colors of the selected h pixels into one of the $k_c$ colors.

11. The apparatus according to claim 10, characterized in that segmenting the urine sample block converted into the Lab color space into a plurality of regions is achieved by using a mean-shift algorithm, wherein the area $A_{min}$ of a minimum region in the urine sample block converted into the Lab color space is adjustable; and     h=ceil (RegionArea/SampleRatio), where RegionArea is the area of a specific region in the plurality of regions after segmentation, h is the number of pixels selected in the specific region, SampleRatio is equal to a specified number of $A_{min}$, and ceil ( ) is a round-up function.

12. The apparatus according to claim 8, characterized in that the approximation unit is further configured to:

convert the block to be processed from an RGB color space into a Lab color space;

calculate an Euclidean distance of the color of the pixel in the block to be processed to the $k_c$ colors respectively; and     approximating the color of the pixel in the block to be processed to a color corresponding to a minimum Euclidean distance in the $k_c$ colors.

13. The apparatus according to claim 8, characterized in that the occurrence frequency correction factor is obtained from a set of training sample blocks, wherein if it is assumed that the number of training sample blocks in the set of training sample blocks is D, and there are $d_i$ training sample blocks containing pixels of the ith color in the code book, then an occurrence frequency correction factor of the ith color idf (i)=log ($D/d_i$); and     the correction unit is further configured to: multiply the number of pixels the color approximation results of which fall on the ith color in the distribution histogram by the occurrence frequency correction factor idf (i) of the ith color.

14. The apparatus according to claim 8, characterized in that the standardization unit is further configured to: take a square root of the corrected number of pixels the color approximation results of which fall on each color in the distribution histogram and then perform standardization.

15. A device for processing a block to be processed urine sediment image, comprising:

a memory for storing an executable instruction; and a processor for performing an operation according to the executable instruction stored in the memory comprising:

approximating the color of a pixel in a block to be processed to one of the $k_c$ colors in a code book, wherein the code book is a set of the $k_c$ colors generated in a set of urine sample blocks, the $k_c$ colors are formed by clustering the colors extracted from the urine sample blocks in the set, and $k_c$ is a positive integer;

obtaining a distribution histogram of the number of pixels the color approximation results of which fall on each color of the $k_c$ colors in the block to be processed;

using an occurrence frequency correction factor to correct the number of pixels the color approximation results of which fall on each color in the distribution histogram;

standardizing the corrected number of pixels the color approximation results of which fall on each color in the distribution histogram; and by way of taking the standardized distribution histogram as a feature in a feature set of block processing, processing the block to be processed.

16. A non-transitory machine-readable medium on which an execute instruction is stored; when the executable instruction executed, a machine is caused to perform an operation comprising:

approximating the color of a pixel in a block to be processed to one of the $k_c$ colors in a code book, wherein the code book is a set of the $k_c$ colors generated in a set of urine sample blocks, the $k_c$ colors are formed by clustering the colors extracted from the urine sample blocks in the set, and $k_c$ is a positive integer;

obtaining a distribution histogram of the number of pixels the color approximation results of which fall on each color of the $k_c$ colors in the block to be processed;

using an occurrence frequency correction factor to correct the number of pixels the color approximation results of which fall on each color in the distribution histogram;

standardizing the corrected number of pixels the color approximation results of which fall on each color in the distribution histogram; and by way of taking the standardized distribution histogram as a feature in a feature set of block processing, processing the block to be processed.

* * * * *